United States Patent [19]

Reddy et al.

[11] Patent Number: 4,840,896

[45] Date of Patent: Jun. 20, 1989

[54] HETEROPOLYMERIC PROTEIN

[75] Inventors: Vermuri B. Reddy, Framingham; Nancy Hsiung, Wellesley; Anton K. Beck, Chestnut Hill; Edward G. Bernstine, Boston, all of Mass.

[73] Assignee: Integrated Genetics, Inc., Framingham, Mass.

[21] Appl. No.: 548,228

[22] Filed: Nov. 2, 1983

[51] Int. Cl.$^4$ .................. C12P 19/00; C12N 5/00; C12N 15/00

[52] U.S. Cl. .................. 435/68; 435/240.2; 435/320; 935/13; 935/70; 935/32

[58] Field of Search .............. 435/68, 70, 71, 172, 435/317, 240, 172.3, 317, 320, 340.2; 935/22, 13, 24, 66, 32, 70; 260/112 R; 530/395

[56] References Cited

U.S. PATENT DOCUMENTS

| | | | |
|---|---|---|---|
| 4,383,036 | 5/1983 | Sugimoto | 435/70 |
| 4,385,586 | 11/1983 | Rubin | 536/27 |
| 4,394,443 | 7/1983 | Weissman et al. | 435/6 |
| 4,401,759 | 8/1983 | Rubin et al. | 435/91 |
| 4,468,464 | 8/1984 | Cohen et al. | 435/317 |

FOREIGN PATENT DOCUMENTS

| | | | |
|---|---|---|---|
| 0078154 | 10/1982 | European Pat. Off. | 435/172.3 |
| 2137631 | 10/1984 | United Kingdom | 435/172.3 |
| 8301783 | 11/1982 | World Int. Prop. O. | 435/172.3 |

OTHER PUBLICATIONS

Hamer et al 1982 "Regulation *In Vivo* of Coloned Mammalian Gene: Cadmium Induces the Transcription . . . ," J. Mol. Appl Gen v1 273–288.

Sarver et al 1981 "Bovine Papilloma Virus DNA: A Novel Eukaryotic Cloning Vector" Mol. Cell Bio v1 486–96.

Pierce et al 1981 "Glycoprotein Hormones: Structure and Function" Ann Rev Biochem v 50 pp. 465–495.

Elder, J. T. et al, *Ann. Rev. Genet.*, vol. 15, pp. 328–330, 1981.

Rice, D. et al, *Proc. Natl. Acad Sci*, vol 79, pp. 7862–7865, 1982.

Lustbader, J. et al, *68th Annual Meeting of the Endocrine Society*, Program and Abstract, Abstract No. 513, Jun., 1986.

Fiddes et al. (1979) Nature 281, 351–6.

Fiddes et al. (1980) Nature 286, 684–687.

Hamer et al. (1983) J. Mol. Applied Gen. 1, 273≧288.

Reddy et al. (1982) Proc. Natl. Acad. Sci. 79, 2064–7.

Kimuri et al., (1972) Virology 49, 394–403.

Pavlakis et al. (1983) Proc. Natl. Acad. Sci. 50, 397–401.

Vamvakopoulos et al. (1980) Proc. Natl. Acad. Sci. 77, 3149–3153.

Rigby (1983) J. Gen. Virol. 64, 255–266.

Morgan et al. (1975) The Journal of Biological Chemistry 13, 5247–5258.

Robert B. Carlsen et al. (1973) The Journal of Biological Chemistry 19, 6810–6827.

Bellisario et al. (1973) The Journal of Biological Chemistry 248(19), 6796–6809.

Moriarty et al. (1981) Proc. Natl. Acad. Sci. 78(4), 2606–2610.

Liu et al. (1982) DNA 1(1), 213–221.

DiMaio et al. (1980) Proc. Natl. Acad. Sci 79, 4030–4034.

Zinn et al. (1982) Proc. Natl. Acad. Sci. 79, 4897–4901.

Burrell et al. (1979) Nature 279, 43–47.

*Primary Examiner*—Jayme A. Huleatt

[57] ABSTRACT

Biologically active heteropolymeric protein composed of a plurality of subunits, each subunit being synthesized by a cell having an expression vector heterologous DNA encoding the subunit.

18 Claims, 10 Drawing Sheets

HETEROPOLYMERIC PROTEIN

BACKGROUND OF THE INVENTION

This invention relates to the use of recombinant DNA techniques to produce heteropolymeric proteins.

Various polypeptide chains have been expressed, via recombinant DNA technology, in host cells such as bacteria, yeast, and cultured mammalian cells. Fiddes, J. C. and Goodman, H. M. (1979) *Nature* Vol. 281, pg. 351–356 and Fiddes, J. C. and Goodman, H. M. (1980) *Nature* Vol. 286, pg. 684–687 describe the cloning of, respectively, the alpha and beta subunits of human choriogonadotropin (hCG).

Kaname U.S. Pat. No. 4,383,036 describes a process for producing hCG in which human lymphoblastoid cells are implanted into a laboratory animal, harvested from the animal, and cultured in vitro; accumulated hCG is then harvested from the culture.

SUMMARY OF THE INVENTION

In general, the invention features, in one aspect, a biologically active heteropolymeric protein composed of a plurality of subunits, each subunit being synthesized by a cell having an autonomously replicating (i.e., not integrated into the chromosone of the host cell) expression vector containing heterologous DNA encoding the subunit.

In preferred embodiments, the protein is synthesized by a eukaryotic cell and the protein is modified post-translationally, most preferably by glycosylation; and the protein is a secreted protein such as a hormone, most preferably a fertility hormone such as hCG, luteinizing hormone (LH) or follicle stimulating hormone (FSH); or the hormone thyroid stimulating hormone (TSH).

In another aspect, the invention features a cell, containing a first expression vector, which cell is capable of producing a biologically active heteropolymeric protein that is encoded at least in part by the vector. In preferred embodiments, a second autonomously replicating expression vector encodes a second portion of the protein or at least two subunits of the protein are encoded by a single expression vector; the protein is hCG or human luteinizing hormone (LH); the vector is a replicating virus or a plasmid; the cell is a monkey or mouse cell; transcription of the different hCG or LH subunits is under the control of the SV40 late promoter; transcription of the alpha subunit of the protein is under the control of the SV40 early promoter and transcription of the beta subunit is under control of the mouse metallothionein promoter, or transcription of both subunits is under the control of the mouse metallothionein promoter; and the expression vector which includes the mouse metallothionein promoter also includes at least the 69% transforming region of the bovine papilloma virus (BPV) genome.

In another aspect, the invention features an autonomously replicating expression vector including two genes encoding two different heterologous proteins, the genes being under the control of two different promoters, most preferably a metallothionein promoter and a BPV promoter; the use of different promoters advantageously minimizes the possiblity of deleterious recombinations.

As used herein, "subunit" refers to a portion of a protein, which portion, or homologue or analogue thereof, is encoded in nature by a distinct in mRNA. Thus, for example, a heavy chain and a light chain of an IgG immunoglobulin are each considered a subunit. Insulin, on the other hand, is composed of two chains which are not considered subunits, because both are, in nature, encoded by a single mRNA, and cleavage into two chains naturally occurs only after translation.

The term "expression vector" refers to a cloning vector which includes heterologous (to the vector) DNA under the control of control sequences which permit expression in a host cell. Such vectors include replicating viruses, plasmids, and phages.

The invention permits the production of a biologically active heteropolymeric protein from a single culture of transformed cells. The production of both subunits of a heteropolymeric protein in the same cell eliminates the necessity of recombining subunits from separate cultures to assemble an active heteropolymeric molecule The system also allows production of proteins, in a single culture, which undergo, in the culture, post-translational modification, e.g. glycosylation and proteolytic processing, for activity or stability.

The use of autonomously replicating expression vectors prevents undesirable influence of the desired coding regions by control sequences in the host chromosone.

Other advantages and features of the invention will be apparent from the following description of the preferred embodiments thereof, and from the claims.

DESCRIPTION OF THE PREFERRED EMBODIMENTS

We turn now to the preferred embodiments of the invention, first briefly describing the drawings thereof.

Drawings

Structure

The cloning vectors of the invention have the general structure recited in the Summary of the Invention, above. Preferred vectors have the structures shown in the Figures, and are described in more detail below.

CONSTRUCTION OF CLONING VECTORS

Isolation of cDNA Clones Encoding the Alpha and Beta Subunits of hCG

All of the techniques used herein are described in detail in Maniatis et al. (1982) *Molecular Cloning: A Laboratory Manual* (Cold Spring Harbor Laboratory), hereby incorporated by reference.

RNA is extracted from placental tissue by the following method. Homogenization of the tissue is carried out in a 1:1 mixture of phenol:100mM Na-acetate (pH 5.5) containing 1 mM EDTA, that has been warmed to 60° for 20 min. After cooling on ice for 10 min., the phases are separated by centrifugation. The hot phenol extraction is repeated twice more followed by two extractions with chloroform.

RNA is precipitated from the final aqueous phase by the addition of 2.5 volumes of ethanol.

In order to enrich for poly A+mRNA, placental RNA is passed over oligo (dT)-cellulose in 0.5 M NaCl buffered with 10 mM Tris-Hcl, pH 7.5, and washed with the same solution. Poly A+mRNA is eluted with 10 mM Tris-HCl (pH 7.5), 1 mM EDTA, 0.05% SDS and precipitated twice with ethanol. Typical initial yields are 1.5–2.0 mg of total RNA per g of tissue, of which about 2% is poly A+mRNA.

Placental cDNA libraries are constructed by reverse transcription of placental mRNA, second strand synthesis using *E. coli* DNA polymerase I (large fragment), treatment with SI nuclease, and homopolymer tailing (dC) with terminal deoxynucleotidyl transferase; all such procedures are by conventional techniques.

In a typical preparation, 20-30% conversion of mRNA to single strand (ss) cDNA; 70% resistance to digestion with nuclease S1 after second strand synthesis; and dC "tails" of ten to twenty-five bases in length, are obtained. These cDNA molecules are then annealed to DNA fragments of the plasmid pBR 322, which has been digested with PstI, and to which dG "tails" have been added. These recombinant plasmids are then used to transform *E coli* cells to generate a cDNA library (transformed cells are selected on the basis of tetracycline resistance).

In order to identify the human alpha hCG clone, a 219 bp fragment of a mouse alpha thyroid stimulating hormone (TSH) clone is used as a hybridization probe. This probe has 77% sequence homology with the human clone. It is radioactively labeled by nick translation and hybridized to the cDNA library under conditions that take into account the extent of homology. Strongly hybridizing clones are analyzed by restriction mapping and clones containing the complete coding sequence of alpha hCG are verified by DNA sequencing.

Construction of Plasmid p alpha SVHVP1

Figure 1:
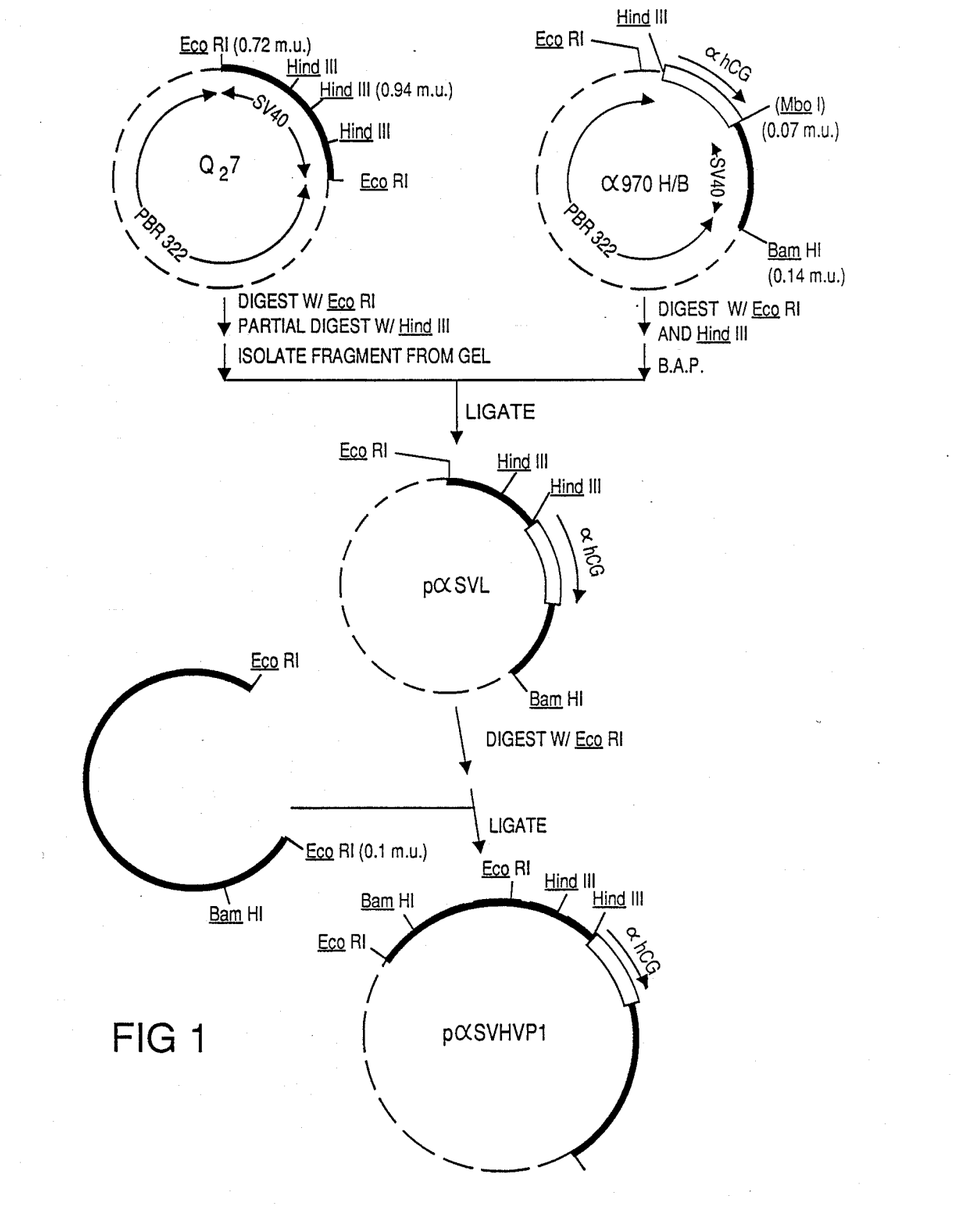
FIG. 1 is a diagrammatic illustration of the construction of the plasmid p alpha SVHVP1, which contains the alpha hCG cDNA clone, portions of SV40 viral DNA, and sequences of the plasmid pBR 322

Referring to FIG. 1, in order to construct the plasmid alpha 970 H/B, a cDNA clone containing the alpha hCG fragment is digested with NcoI. The NcoI site, just 5' to the ATG codon signalling initiation of translation, is filled in and ligated to a synthetic HindIII linker. Similarly, the natural HindIII site in the 3' untranslated region of the clone is cut, filled in with *E coli* DNA polymerase Klenow, and then ligated to a synthetic BamHI linker. This fragment is cloned into the plasmid pBR 322 between its HindIII and BamHI sites to generate the plasmid alpha 574 H/B. This plasmid is digested with BamHI, treated with alkaline phosphatase, and ligated to the 396 bp Sau3A fragment of SV40 DNA (from 0.07 to 0.14 map units) which has been isolated from a polyacrylamide gel. The ligation mix is used to transform *E. coli* to ampicillin resistance and the desired plasmid, alpha 970 H/B, is identified among the transformants.

The plasmid $Q_27$ is constructed by cutting SV40 at its HpaII site, making flush ends by digestion with nuclease S1, ligating on Eco RI linkers, digesting with EcoRI, and cloning the resulting 1436 bp fragment into the EcoRI site of pBR 322.

Referring to FIG. 1, $Q_27$ is digested completely with EcoRI and partially with HindIII; the fragment from 0.72 to 0.94 map units is isolated and cloned into alpha 970 H/B, which has been digested with EcoRI and HindIII and treated with alkaline phosphatase. The ligation mix is used to transform *E. coli,* and the desired plasmid, p alpha SVL, is identified among the transformants by restriction mapping.

p alpha SVL is digested with EcoRI and the fragment of SV40, with EcoRI ends, extending from 0 to 0.72 map units, and containing the SV40 origin of replication and the intact early region, is ligated to it to generate the plasmid p alpha SVHVP1, which is isolated from *E. coli* transformants.

Construction of Plasmid p beta SVVP1

Figure 2:
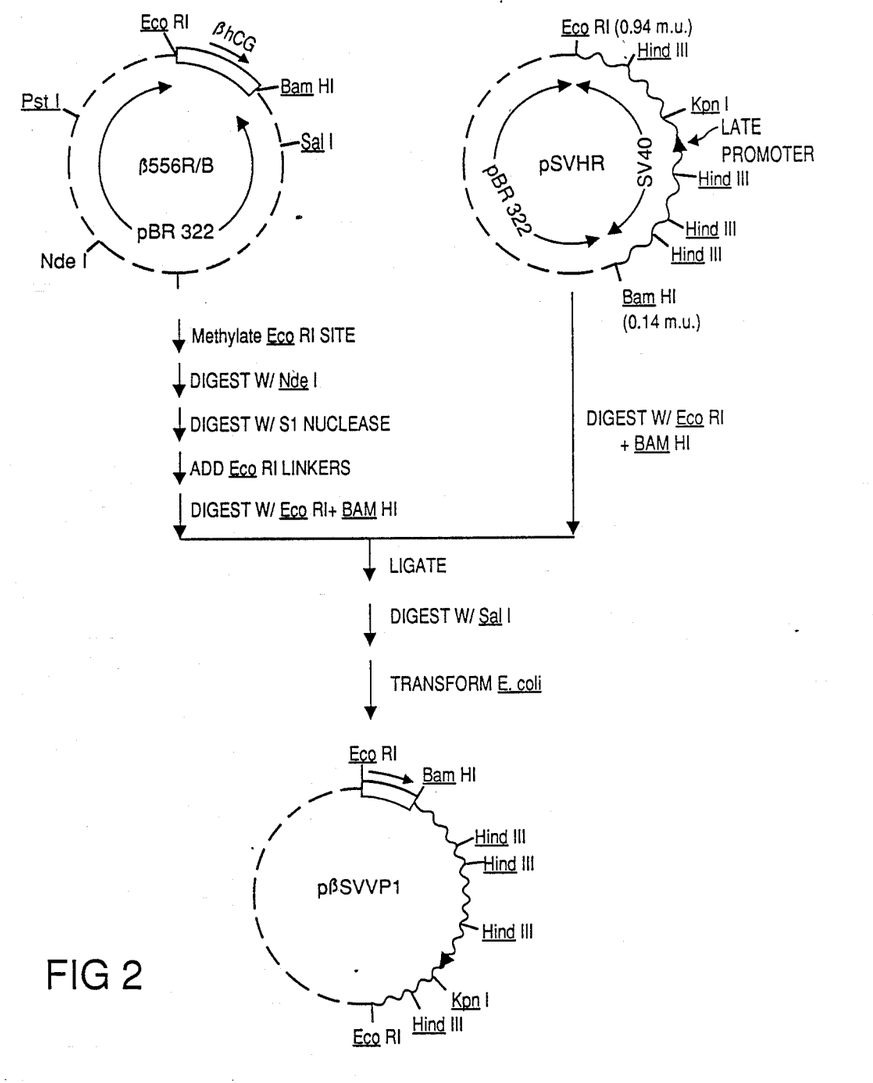
FIG. 2 is a diagrammatic illustration of the construction of plasmid p beta SVVP1, which incorporates the beta hCG cDNA clone, regions of SV40 DNA and a portion of pBR 322 including the region conferring resistance to ampicillin on host *E. coli.*

A 579 bp cDNA clone coding for beta hCG was obtained from John C. Fiddes at Cold Spring Harbor Laboratory, Cold Spring Harbor, N.Y. (Fiddes et al (1980) Nature Vol. 286, pg. 684–687). T is fragment is ligated at each end to synthetic BamHI linkers. After digestion by HoaI restriction enzyme, the ends are filled in with Klenow DNA polymerase and synthetic EcoRI linkers are ligated on so that an EcoRI site is about 10 bp 5' to the ATG codon of the signal peptide coding sequence. A BamHI site is about 60 bp 3' to the non-sense codon marking the end of the coding sequence. Referring to FIG. 2 this 556 bp EcoRI-BamHI fragment is isolated and cloned into pBR 322, between the EcoRI and BamHI sites to give the plasmid p beta 556 R/B.

In order to construct the plasmid PSVHR (FIG. 2), SV40 DNA is partially digested with HindIII to yield linear molecules, digested with nuclease S1 to make flush ends, ligated to synthetic EcoRI linkers and digested with EcoRI and BamHI. The fragment from 0.94 to 0.14 map units, containing the SV40 origin of replication and early region, is cloned into pBR 322 as an EcoRI-BamHI piece.

Referring still to FIG. 2, the EcoRI site of the plasmid p beta 556 R/B is methylated in a reaction catalyzed by EcoRI methylase, following which the plasmid is cut with NdeI. EcoRI linkers are ligated to the SI treated NdeI flush ends and activated by digestion with EcoRI, which is followed by digestion with BamHI.

The SV40 fragment of pSVHR from the EcoRI site to the BamHI site is isolated and ligated in a reaction mix containing the digestion fragments of p beta 556 R/B. Following ligation, the mix is digested with SalI to eliminate plasmids which have re-inserted the EcoRI (NdeI) to BamHI piece of pBR 322. *E. coli* is transformed with the digested ligation mix and p beta SVVP1 is identified and isolated.

Construction of the Plasmid p Alpha Beta SVVP1

Figure 3:
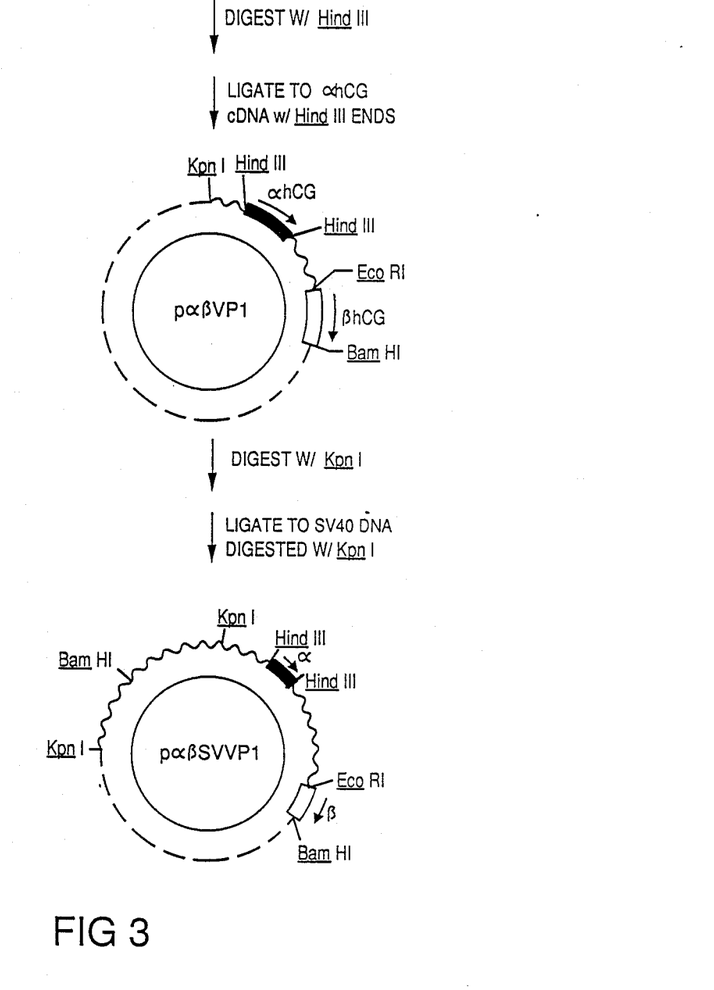
FIG. 3 is a diagrammtic illustration of the construction of the plasmid p alpha beta SVVP1 in which the alpha and beta hCG cDNA clones are inserted into SV40 DNA.

Referring to FIG. 3, pBR 322/Kpn is derived from pBR 322 by inserting a KpnI linker into its unique EcoRI site, after this site is deleted by digestion with EcoRI, followed by digestion with S1 nuclease.

Referring still to FIG. 3, SV40 DNA is digested with AvaII. The staggered ends of the resulting fragments are filled in by Klenow DNA polymerase to form flush ends, and the mixture is then fractionated on a polyacrylamide gel. The 682 base pair fragment (0.64 to 0.77 map units) containing the origin of replication and the unique KpnI site is isolated from the gel, ligated to synthetic HindIII linkers, and digested with HindIII and KpnI.

The resulting fragments are ligated to pBR 322/Kpn. p266, which contains the 266 base pair KpnI HindIII fragment, including the SV40 late promoter region, is isolated. p266 is cut with HindIII and BamHI, and treated with bacterial alkaline phosphatase.

Still referring to FIG. 3, p beta SVVPI/B is constructed as follows: p beta SVVPI (FIG. 2) is cut with EcoRI, followed by ligation to eliminate pBR 322 sequences. Subsequently, this DNA is cut with BamHI and cloned into the BamHI site of pBR 322.

The resulting plasmid, p beta SVVPI/B, is then digested with HindIII and BamHI and the 1003 base pair HindIII-BamHI fragment is ligated into p266 to yield the plasmid p beta VP1 266, in which the beta hCG cDNA is positioned downstream from the SV40 late promoter in such a way that its RNA transcript would be spliced as if it were the viral VP1 transcript.

The alpha hCG cDNA is inserted into p beta VP1 266 as a HindIII fragment, which has been cut at its HindIII site and treated with bacterial alkaline phosphatase. *E. coli* transformants derived from this ligation are screened by restriction mapping, and plasmids are isolated that have the desired structure, in which the alpha hCG cDNA has replaced VP2 in the correct orientation, followed downstream by the beta hCG cDNA, which has replaced VP1.

One such isolated plasmid, p alpha beta VP1, is used to complete the construction of p alpha beta SVVPl. The plasmid is cut with KpnI, and the full SV40 genome, cut with KpnI, is inserted by ligation into this site. Following transformation of *E.. coli*, a plasmid with the required structure, p alpha beta SVVPl, is isolated. This plasmid contains DNA encoding both the alpha and beta subunits of hCG, and thus is capable of directing the expression, in host mammalian cells, o both subunits, whereby biologically functional, glycosylated heterodimeric hCG is produced (glycosylation occurs post-translationally).

Construction of Plasmids pRF 375 and pRF 398

Figure 4:
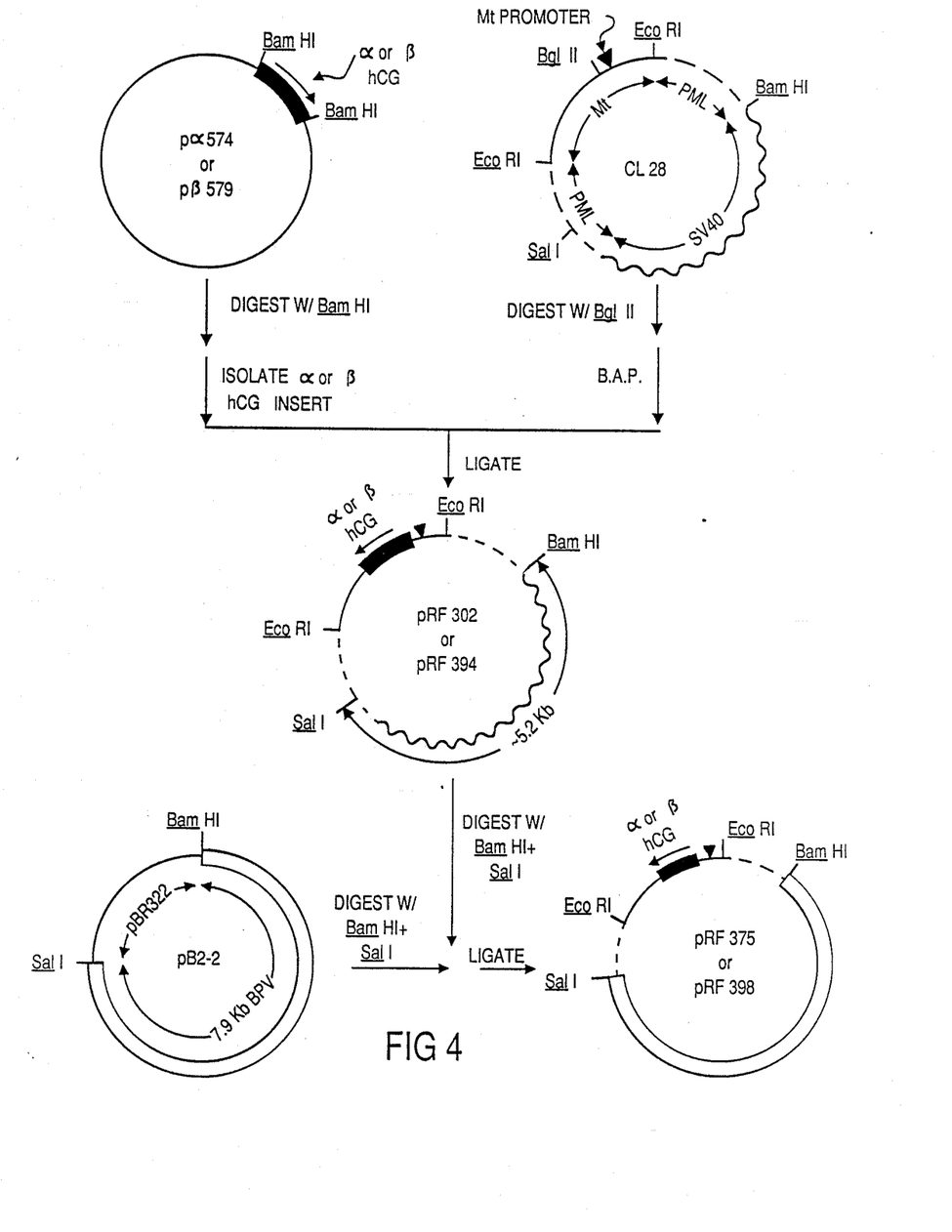
FIG. 4 is a diagrammtic illustration of the construction of the plasmids pRF375 and pRF398.

Referring to FIG. 4, the plasmid CL28 (identical to plasmid JYMMT(E); Hamer et al. (1983) J. Mol. Applied Gen. 1, 273–288), containing the murine metallothionein promoter, SV40 DNA, and pBR 322 sequences, is cut with the restriction endonuclease Bql II. At this site are inserted cDNA clones of either alpha hCG or beta hCG, containing untranslated regions of about 10 and 30 bp at their 5' and of about 220 and 60 bp at their 3' ends. These clones have been genetically engineered by the addition of synthetic Bam HI linkers at their termini.

The resulting plasmids pRF 302 (alpha) or pRF 394(beta) are digested with restriction enzymes BamHI and SalI to release the SV40 DNA sequences.

Plasmid pB2-2, which contains the entire BPV genome, and some pBR 322 sequences, is digested with BamHI and SalI to yield the BPV genome with BamHI/SalI ends; this fragement is ligated into pRF 302 (alpha) and pRF 394 (beta) containing the metallothionein-hCG sequences.

Following transformation of *E. coli,* plasmids pRF 375 and pRF 398 are identified and isolated. They encode alpha hCG or beta hCG, respectively, under the control of the mouse metallothionein promoter.

Construction of the Plasmid RF 398 alpha t2

Figure 5:
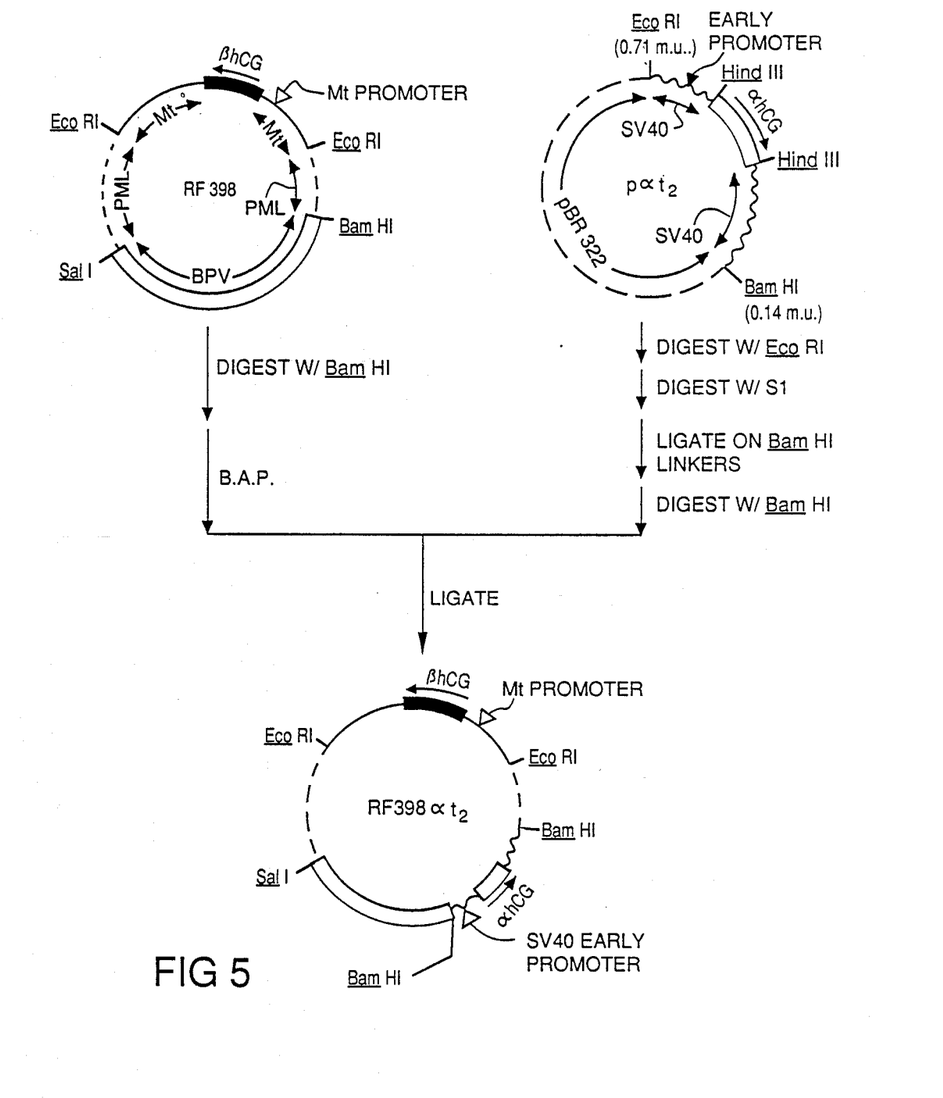
FIG. 5 is a diagrammatic illustration of the construction of the plasmid RF398 alpha $t_2$.

Referring to FIG. 5, the plasmid p alpha $t_2$ is derived by cloning the alpha hCG 574 HindIII fragment into plasmid pVBt2 (V.B. Reddy et al., PNAS 79, 2064–2067, 1982). p alpha $t_2$, which contains the alpha hCG cDNA under the control of the SV40 early promoter, is digested with EcoRI. The 5' overhangs are removed by S1 nuclease digestion prior to the addition of synthetic BamHI linkers by blunt end ligation.

Plasmid RF 398 (FIG. 4) is digested with BamHI and treated with bacterial alkaline phosphatase. The 1735 base pair BamHI fragment of p alpha $t_2$ is inserted in to RF 398. The resulting plasmid RF 398 alpha $t_2$ is isolated from *E. coli* transformants. This plasmid thus has the beta hCG cDNA in a transcriptional unit under control of the mouse metallothionein promoter and the alpha hCG cDNA in a transcriptional unit controlled by the SV40 early promoter.

Expression of Luteinizing Hormone (LH) cDNA Clones Construction of a Human Pituitary cDNA Library RNA is prepared from human pituitaries by homogenizing 5 to 10 grams of the frozen glands in 20 ml of a solution containing 4 M guanidine thiocyanate, 1 M 2-mercaptoethanol, 0.05 M Na-acetate (pH 5.0), and 0.001 M EDTA. One g CsCl is added per ml of homogenate and the suspension is centrifuged at 2,000 rpm for 15 min. The supernatant is layered carefully over a 15 ml cushion of CsCl solution (containing 1.25 ml of 1 M Na-acetate (pH 5), 62.5 microliters of 0.4 M EDTA and 39.8 g of CsCl in a final volume of 35 ml) and centrifuged at 45,000 rpm in the Ti 70 rotor of a Beckman ultracentrifuge for 18–24 h at 20° C. The RNA visible as a pellicle in the gradient is removed with a syringe, diluted, and precipitated by the addition of two volumes of ethanol. Following three cycles of dissolution and reprecipitation, the RNA pellet is dissolved in $H_2O$ and brought to 0.01 M Tris-HCl (pH 7.5) and 0.5 M NaCl by the addition of concentrated stock solutions. The preparation is then enriched for poly $A^+$ mRNA by two passes over oligo dT-cellulose, as described above in the case of placental RNA.

A human pituitary cDNA library is constructed from the poly $A^+$ mRNA as described above for placental poly $A^+$ mRNA except that both the large fragment *E. coli* DNA polymerase I and the avian myeloblastosis virus reverse transcriptase are used sequentially for second strand cDNA synthesis. Reverse transcriptase is used first. The reaction is stopped by phenol extraction. The aqueous phase of the centrifuged extract is applied to a 5 ml column of BioGel A-5m. Fractions containing high molecular weight material are pooled, concentrated, precipitated with two volumes of ethanol, dried, and dissolved in 100 mM Tris-HCl (pH 8.3), 10 mM MgCl$_2$, 140 mM KCl, 20 mM 2-mercaptoethanol, 1 mM of each of the four deoxyribonucleoside triphosphates, for reverse transcription. Reverse transcriptase is added to about 20 units per microgram of cDNA. Double stranded cDNA is then treated with nuclease S1, tailed, and cloned as described above.

Isolation of Beta LH cDNA Clones

Figure 6:
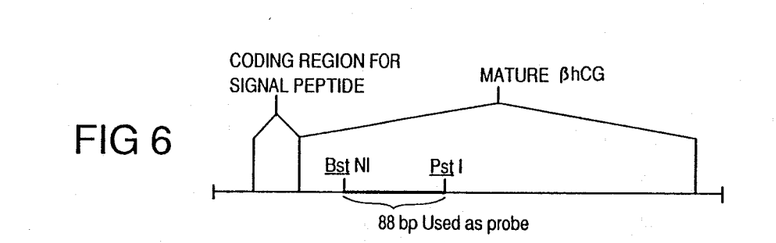
FIG. 6 is a diagram illustrating the location of an 88 bp probe within the beta hCG cDNA clone

Colonies grown on nutrient agar plates containing 25 micrograms per ml of tetracycline are transferred to nitrocellulose filters. Colonies are lysed in situ by treatment with 0.5 M NaOH and neutralized with 0.5 M Tris-HCl (pH 7.4) containing 1.5 M NaCl. Liberated DNA is fixed to the filter by baking at 80° C. in a vacuum oven for 2 h. The filters are screened by hybridization to a $^{32}$P labeled 88 base pair fragment of the beta hCG clone corresponding to amino acids 16 to 45 of the mature hCG beta chain, which has 29 of 30 amino acids in common with this region of the beta LH polypeptide (FIG. 6). Hybridization is carried out overnight at 32° in 50% formamide, 0.75 M NaCl, 0.075 M Na-Citrate (pH 7.0), 2.5% dextran sulfate, 0.1% polyvinylpyrollidone, 0.1 mg per ml bovine serum albumin, and at least $10^5$ cpm per filter of $^{32}$p-labeled 88 bp beta hCG fragment. Filters are washed several times in 0.15 M NaCl, 0.015 M Na-citrate at 7° C. before autoradiography. One of the positive isolated clones LH12 (FIG. 7), is used further. LH12 is 365 bp long and includes sequences coding for 15 amino acids of the pre-beta signal sequence plus 105 amino acids of the mature beta LH polypeptide. Its nucleotide sequence is determined. Since the complete mature beta LH is not coded by LH12, further screening of the human pituitary cDNA library is carried out using a 240 bp NcoI-PvuII fragment of LH12 (FIG. 7) as a $^{32}$P labeled hybridization probe. The clone LH6 (FIG. 7) is isolated from this screening. LH6 contains the complete 3' end of beta LH, including the region corresponding to the untranslated portion of the mRNA through 27 A residues of the poly A "tail" of the mRNA. No clones are found that extended further than LH12 in the 5' direction. DNA sequencing of the complete, combined mature beta LH coding regions reveals two differences in the amino aci sequence of beta LH from the published protein sequence data: position 42 is a methionine and position 55 is a valine. Also, the mature beta LH contains 121 amino acids, based on the cDNA sequence.

Figure 7:
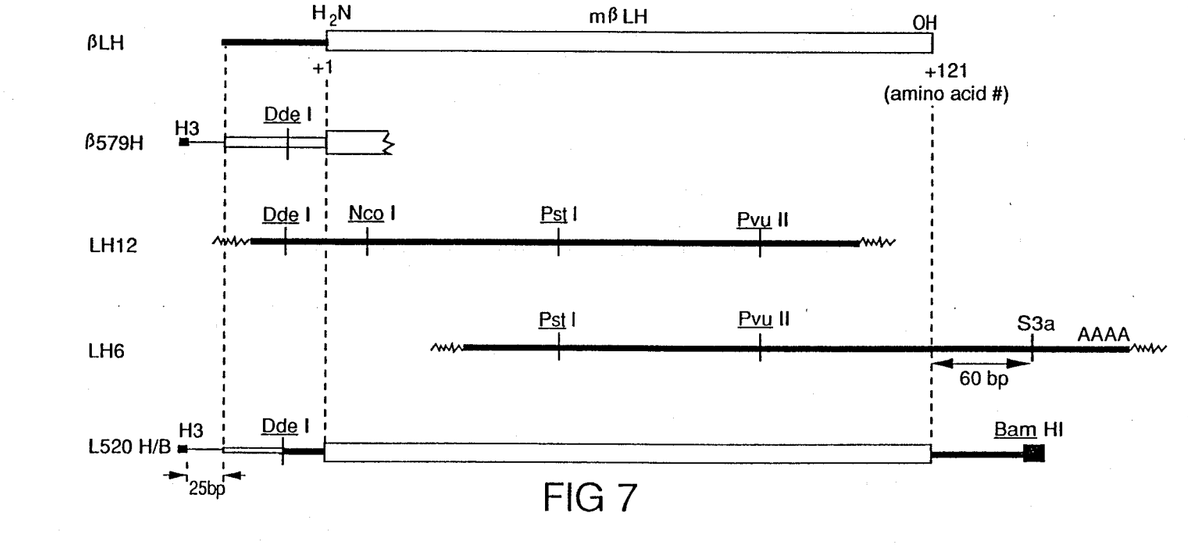
FIG. 7 illustrates the beta LH restriction map, and the pieces used in the construction shown in FIG. 8.
Figure 8:
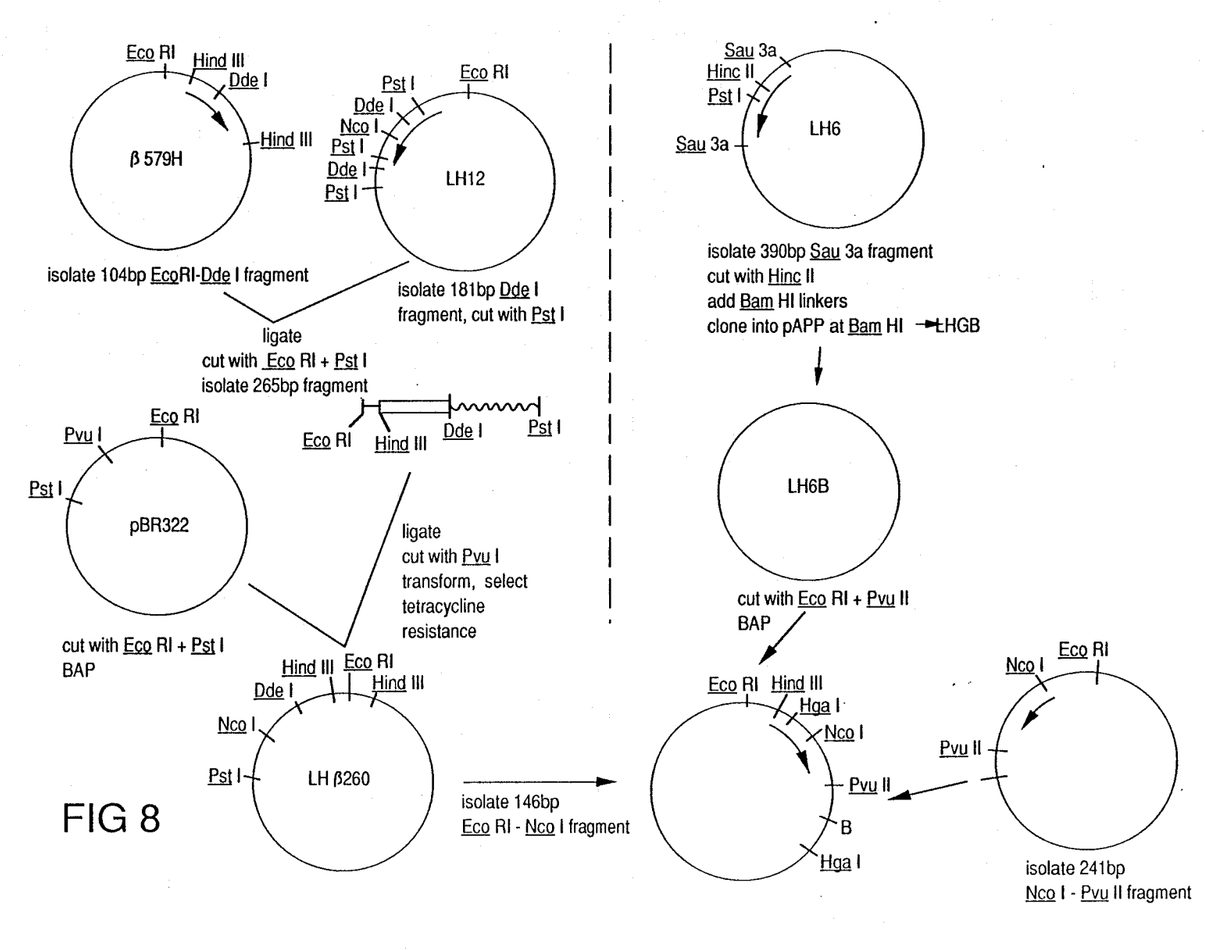
FIG. 8 is a diagrammatic illustration of the construction of a plasmid, LH520H/B, containing the complete mature beta LH cDNA clone.

A clone containing an intact signal peptide coding sequence and the complete mature beta LH sequence is constructed as shown in FIG. 8, using the restriction fragments illustrated in FIG. 7. A 104 bp EcoRI-DdeI fragment is isolated from the plasmid beta 579 H and ligated to an isolated 181 bp DdeI fragment, subsequently digested with PstI, from the LH12 plasmid. Following ligation overnight at 15° C., the ligation mix is digested with EcoRI and PstI and fractionated on a 7% polyacrylamide gel from which the desired 256 bp fragment is isolated. This fragment fuses the beta hCG signal sequence to that of the pre-beta LH in such a way as to provide a coding sequence for a 20 amino acid signal peptide.

The 256 bp EcoRI-PstI fragment is cloned into pBR 322 digested with EcoRI and PstI so as to give the plasmid LH beta 260. The 146 bp EcoRI-NcoI fragment indicated in FIG. 8 is isolated from a polyacrylamide gel and used later in the construction as described below.

The LH6 plasmid (FIG. 8) is digested with Sau3a and the 390 bp fragment is isolated by polyacrylamide gel electrophoresis. This fragment is then digested with HincII, ligated to BamHI linkers, digested with BamHI, and cloned into the plasmid pAPP at the BamHI site. pAPP is derived from pBR 322 by digestion with AvaI, filling in the 5' overhang with the dNTP's and the large fragment DNA polymerase I of E. coli, digestion with PvuII, and ligation to close the plasmid so as to eliminate the PvuII site. The plasmid LH6B, isolated from the ligation of the 340 bp BamHI fragment into the BamHI site of pAPP, is digested with EcoRI and PvuII, and treated with bacterial alkaline phosphatase. The fragments are ligated to a mixture of the 145 bp EcoRI-NcoI fragment of LH beta 260, described above, and the isolated 241 bp NcoI-PvuII fragment from the plasmid LH12 shown in FIG. 8. The ligation mix is used to transform E. coli to ampicillin resistance. The plasmid LH 520 H/B is found among the transformants. LH 520 H/B contains a complete beta LH coding seguence including a hybrid signal peptide seguence.

Construction of p Alpha LHSVVP1

In order to express this pre-beta LH clone in an SV40-based vector as had been done for the pre-alpha and pre-beta hCG clones described previously, it is desirable to place an EcoRI site very close to the ATG of the pre-beta coding seguence. This is accomplished by digesting LH520 H/B with HgaI filling in the 5' overhang, ligating on synthetic EcoRI linkers, digesting with EcoRI and BamHI, and cloning the isolated 496 bp EcoRI-BamHI fragment into pBR 322 digested with EcoRI and BamHI and treated with bacterial alkaline phosphatase. The plasmid pLH496 R/B is isolated from E. coli transformed with this ligation mix and is used as the the source of the 496 bp fragment to be expressed.

Figure 9:
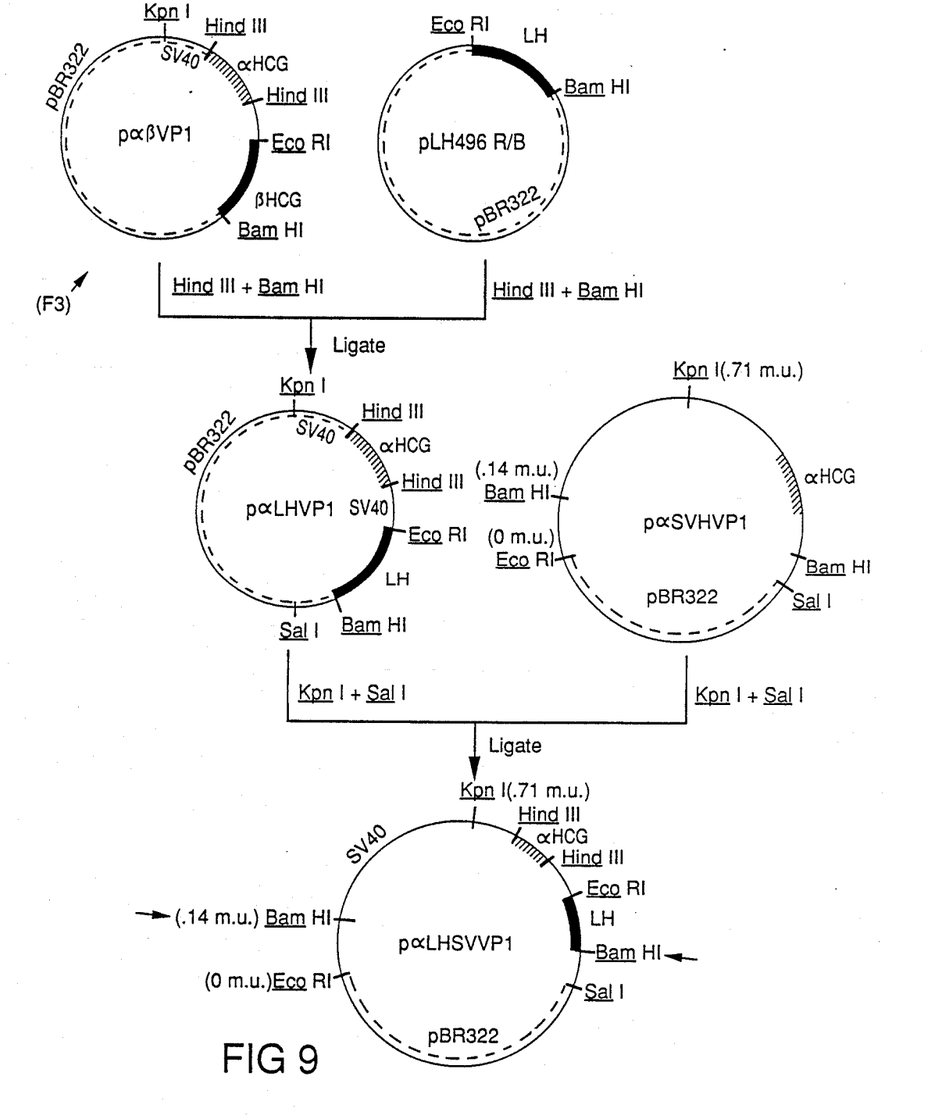
FIG. 9 is a diagrammatic illustration of the construction of the viral vector p alpha LHSVVP1.

The plasmid p alpha beta VP1, whose construction and use in expressing both subunits of hCG is described earlier (FIG. 3); is digested with EcoRI and BamHI and ligated in a reaction mix containing the plasmid pLH496 R/B which had been digested with both of these enzymes (FIG. 9). The plasmid p alpha LHVP1 is identified among the E. coli transformants. As shown in FIG. 9, the intact SV40 viral early region is taken from p alpha SVHVP1 (FIG. 1) and inserted by ligation as a KpnI-SalI fragment into p alpha LHVP1 which had been digested with KpnI and SalI to give the plasmid p alpha LHSVVP1. By cutting this plasmid with BamHI and religating, the virus alpha LHSVVP1 is formed. This virus contains cloned cDNA's for the common (to LH and hCG, as well as FSH and TSH) alpha subunit and the specific beta LH subunit under control of the SV40 late promoter. The cloned cDNA's are positioned in such a way that the common alpha insert replaced the viral VP1 protein coding seguence and the beta LH insert replaced the viral VP2 coding seguence.

Figure 10:
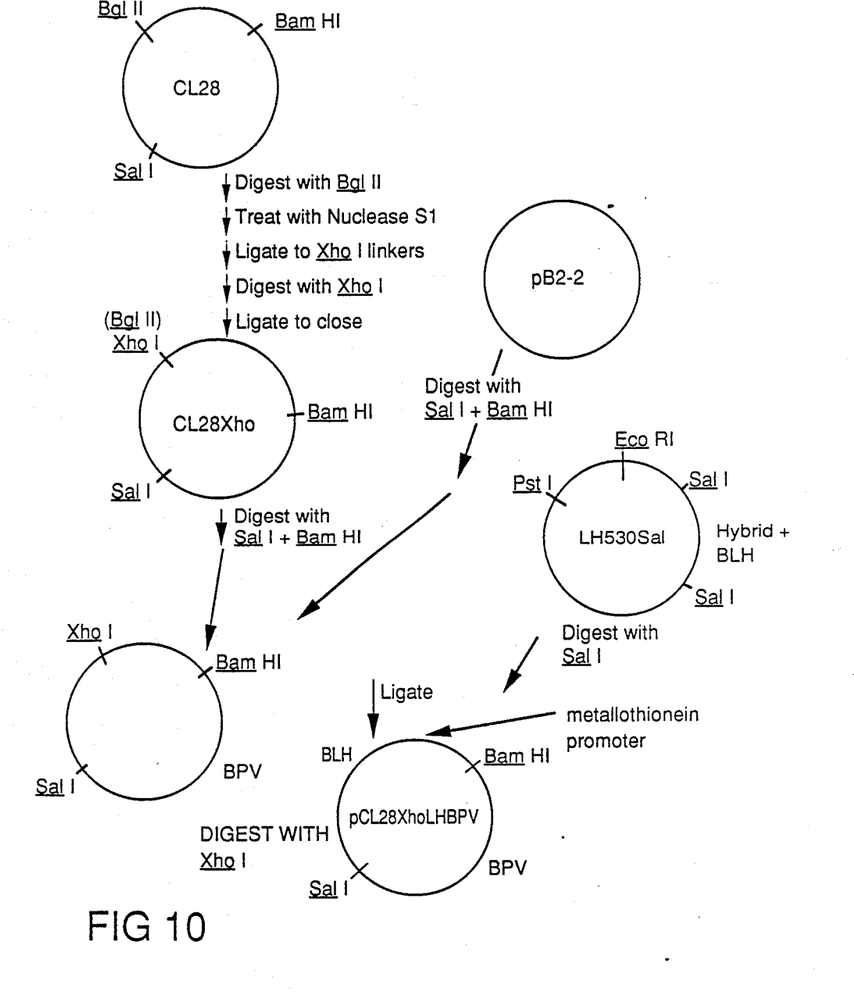
FIG. 10 is a diagrammatic illustration of the construction of the BPV-containing plasmid pCL28XhoLHBPV, encoding the beta subunit of LH.

Insertion of the Beta LH cDNA (With Beta hCG 5' End of Signal Peptide) into a BPV-Based Expression System LH 520 H/B (FIG. 8) is digested with HindIII and BamHI, treated with the E. coli DNA polymerase (Klenow); ligated to synthetic SalI linkers, digested with SalI, and cloned into the SalI site of pBR 322. The resulting plasmid, LH 530 Sal, is used as a source of the LH cDNA clone for insertion into the mouse metallothionein gene of the plasmid CL28 as described in FIG. 10.

CL28 is cut with BglII, treated with nuclease S1, and ligated to XhoI linkers. Following digestion with XhoI, ligation and digestion with BglII, E. coli is transformed with the reaction mix to give the plasmid CL28Xho. This plasmid is digested with BamHI and SalI and ligated to a BamHI plus SalI digest of the plasmid pB2-2 (FIG. 4) to give the plasmid CL28XhoBPV. The latter LH insert is then ligated into the XhoI site of CL28XhoBPV as a SalI fragment, since the 5' overhang of SalI digests is complementary to that of XhoI digests. Following digestion with XhoI to eliminate background, E coli is transformed and the desired plasmid pCL28XhoLHBVP containing the (hybrid) pre-beta LH insert, in a BPV-based plasmid, under control of the mouse metallothionein promoter, is isolated.

Transfection and Infection of Host Monkey Cells

The incorporation of virus-containing vectors into eukaryotic cells for the production of a heteropolymeric protein is generallY accomplished as follows. First, if the viral DNA and homopolymeric protein-encoding DNA are incorporated into a plasmid, which is maintained, in, say, E. coli, the plasmid seguences (e.g. the PBR 322 seguences) are removed and the resulting DNA is ligated to form circular DNA including the viral region and the heteropolymeric protein-encoding seguence or seguences. This circular DNA generally does not contain all of the genetic information needed to produce a replicating virus, the other necessary seguences (e.g. those encoding coat protein) having been replaced by the heteropolymeric protein-encoding sequence or sequences. The circular DNA, minus the plasmid DNA, must be close enough in size to the naturally occurring viral DNA from which it is derived to permit the DNA to enter and replicate in appropriate host mammalian cells.

The circular DNA is used to transfect host cells in order to produce virus stock for later infections. Since some of the DNA necessary to produce virus is missing, the transfection must occur in conjunction with helper virus DNA encoding enough of the missing function to produce replicating virus.

Transfected host cells are grown and incubated until lysed by replicating virus. The resulting replicating virus stock, including helper virus, is then used to infect host cells for production of the heteropolymeric protein. Virus stock is maintained, since it generally needs to be reused to infect fresh batches of host cells, as each culture of infected, protein-producing host cells generally is eventually lysed by the virus The specific recombinant DNA sequences described above are used to transfect, and then infect, host cells, as follows.

The pBR 322 sequences are removed from the above-described SV40-containing plasmids to produce transfecting viral DNA. In the case of p alpha SVHVP1 and p alpha beta SVVPI, this is accomplished by digestion with BamHI, followed by ligation under conditions favoring circularization of the fragments to give (among other products) alpha SVHVP1 and alpha beta SVVPI. For p beta SVVPI digestion with EcoRI followed by re-ligation brings the SV40 late promoter and VP1 splice region into juxtaposition with the beta hCG cDNA insert at the same time that it eliminates pBR 322 sequences and forms beta SVP1. At the same time, ptsA58 Bam (tsA58 SV40 viral DNA cloned into the pBR 322 BamHI site) is cut with BamHI and ligated to obtain self-ligated circles. Analogous methods are used for the LH vectors. Separate virus stocks are prepared as described below.

The DNA's, which are cut and ligated as described above, are ethanol precipitated and dissolved in sterile water. Approximately 1 ug of PtsA58 Bam DNA (helper virus) and 10 ug of recombinant DNA (encoding alpha and/or beta hCG or LH) are combined in a sterile test tube, mixed with 2 ml of TBS buffer (G. Kimura and R. Dulbecco 1972, Virogy, 49, 79–81) and 1 ml of 2 mg/ml DEAE-dextran solution and added to a monolayer of confluent monkey CV-1 cells previously washed twice with 10 ml of TBS in a T-75 flask. The cells are left at 37° C. for 1-2 hrs with occasional shaking, washed with TBS twice, fed with 10 ml of DMEM containing 5% fetal calf serum, and left at 40° C. for 10-15 days. After complete cell lysis, the medium is transferred to a test tube, frozen and thawed five times, and centrifuged at 3000 rpm for five minutes. The resulting supernatants serve as virus stocks for infection of fresh CV-1 cells.

To accomplish an infection, CV-1 cells are grown to confluence in a T-150 flask. 1 ml of one of the virus stocks (made as described above) is added to the flask and the cells are incubated at 40° C. for 5 days.

For mixed infections, CV-1 cells are grown to confluence in a T-150 flask. alpha SVHVP1 and beta SVVP1 viruses are mixed in a 1:1 ratio and 1 ml of the mixed virus is used to infect CV-1 cells at 40° C.

Transfection of Mouse Cells

To produce heterodimeric hCG using a mixed transfection, five ug of each BPV plasmid, i.e., pRF 375 (alpha hCG) and pRF 398 (beta hCG), are mixed and added to 0.5 ml of a 250 mM CaCl$_2$ solution containing 10 ug of salmon sperm DNA as carrier. This mixture is bubbled into 0.5 ml of 280 mM NaCl, 50 mM Hepes and 1.5 mM sodium phosphate. The calcium phosphate precipitate is allowed to form for 30-40 minutes at room temperature.

24 hours prior to transfection, $5 \times 10^5$ cells of mouse C127 cells (available from Dr. Dean Hamer, National Cancer Institute, NIH, Bethesda, Md.) are placed in a 100 mm dish or T-75 flask. Immediately before adding the exogenous DNA, the cells are fed with fresh medium (Dulbecco's Modified Medium, 10% fetal calf serum). One ml of calcium phosphate precipitate is added to each dish (10 ml), and the cells are incubated for 6-8 hours at 37° C.

The medium is aspirated and replaced with 5 ml of 20% glycerol in phosphate buffered saline, pH 7.0 (PBS) for 2 minutes at room temperature. The cells are washed with PBS, fed with 10 ml of medium, and incubated at 37° C. After 20-24 hours, the medium is changed and subseguent refeeding of the cells is carried out every 3-4 days. Individual clones are grown in T-25 cm flasks. After 7-21 days, cell clones can be transferred to larger flasks for analysis.

To produce heterodimeric hCG using a single transfection, plasmid RF 398 alpha $t_2$ is employed in the same manner as the above two plasmids were employed for a mixed infection.

To make heterodimeric LH, plasmids PRF 375 and pCL28XhoLHBPV are mixed, as described above in the case of hCG.

An interesting observation is that culturing cells containing beta hCG or beta LH-encoding vectors alone, in the absence of alpha-encoding cells, produces practically no beta subunit, while cells containing alpha and beta-encoding sequences produce not only heterodimer, but free beta subunit as well. This lends support to the notion that the production of both subunits in a single cell culture has the additional advantage of somehow permitting the presence of the alpha subunit to stabilize the beta subunit.

Deposits

The following, described above, have been deposited in the American Type Culture Collection, Rockville, Md.:

alpha beta SVVP1, ATTCVR2077;
alpha SVHVP1, ATCCVR2075;
beta SVVP1, ATCCVR2075;
pRF 375 in C127 cells, ATCCCRL8401;
pRF 398 in C127 cells, ATCCCRL8401;
pCL28XhoLHBPV *E. coli*, ATCC39475;
pRF 398 alpha $t_2$ in C127 cells, ATCCCRL8400.

Use

The transformed cell lines of the invention are used to produce biologically active heteropolymeric proteins. hCG made according to the invention, for example, has a number of well-known medical uses associated with human fertility.

Other Embodiments

Other embodiments are within the following claims. For example:

Other heteropolymeric proteins, e.g., follicle stimulating hormone, or thyroid stimulating hormone, can be produced, as can human or animal immunoglobulins or immune response antigens It may not be necessary that the heteropolymeric protein be produced by one cell, or even in one culture. One alternative is to co-culture two cells, one of which produces one subunit and the other of which produces the other subunit; the secreted subunits can then associate in the medium to form heterodimer. Another alternative is to employ separate cultures, each producing a different subunit, and then to combine the culture media from them to permit association into heteropolymer.

Other host cells, vectors, promoters, transforming sequences, and viruses can also be employed. The host cell employed generally is dependent on the vector being used. For example, when the vector is replicating virus or non-replicating viral DNA, the host cells are cells capable of being infected or transfected, respectively, by those vectors; e.g., SV40-containing vectors require monkey host cells, preferably CV-1 cells. Where the cloning vector is a plasmid having procaryotic control sequences, prokaryotic host cells, e.g., *E. coli*, are used. Where the cloning vector is a plasmid having eukaryotic control sequences, appropriate eukaryotic host cells, e.g., mouse C127 cells, are used.

We claim:

1. A mammalian cell comprising a first expression vector, said cell being capable of producing a biologically active heterodimeric human fertility hormone comprised of an alpha subunit and a beta subunit, each said subunit being encoded in nature by a distinct mRNA, said hormone being selected from the group consisting of hCG, and LH, the alpha subunit of said hormone being encoded by said first expression vector and the beta subunit being encoded by said first expression vector or a second expression vector.

2. The cell of claim 1, further comprising a second expression vector encoding the beta subunit of said hormone.

3. The cell of claim 2, said second expression vector being autonomously replicating.

4. The cell of claim 1, said first vector being a plasmid.

5. The cell of claim 4, said cell being a monkey cell.

6. The cell of claim 1, the alpha and beta subunits of sid heterodimeric hormone being encoded by said first expression vector.

7. The cell of claim 6, transcription of said alpha and beta subunits of said heterodimeric hormone being under the control of the SV40 late promoter.

8. The cell of claim 6, transcription of the alpha subunit of said heterodimeric hormone being under the control of the SV40 early promoter, and transcription of the beta subunit of said heterodimeric hormone being under the control of the mouse metallothionein promoter.

9. The cell of claim 8, said first vector comprising at least the 69% transforming region of the bovine papilloma virus genome.

10. The cell of claim 1, transcription of the alpha and beta subunits of said heterodimeric hormone being under the control of the SV40 late promoter.

11. The cell of claim 1, transcription of the alpha and beta subunits of said heterodimeric hormone being under the control of the mouse metallothionein promoter.

12. The cell of claim 1, said cell being a mouse cell.

13. The cell of claim 1, said first expression vector being autonomously replicating.

14. A method for producing the biologically active human fertility hormone LH comprising culturing host mammalian cells comprising a first expression vector encoding the beta subunit of said LH and a second expression vector encoding the alpha subunit of said LH.

15. The method of claim 14, wherein each said expression vector is autonomously replicating.

16. A method for producing biologically active hCG comprising culturing host mammalian cells comprising an expression vector encoding the alpha and beta subunits of said hCG.

17. A method for producing biologically active hCG comprising culturing host mammalian cells comprising a first expression vector encoding the alpha subunit of said hCG and a second expression vector encoding the beta subunit of said hCG.

18. A method for producing the biologically active human fertility hormone LH comprising culturing host mammalian cells comprising an expression vector encoding both the beta and alpha subunits of said LH.

* * * * *

UNITED STATES PATENT AND TRADEMARK OFFICE
CERTIFICATE OF CORRECTION

PATENT NO. : 4,840,896

DATED : June 20, 1989

INVENTOR(S) : Vermuri B. Reddy et al.

It is certified that error appears in the above-identified patent and that said Letters Patent is hereby corrected as shown below:

On the face of the patent, under "OTHER PUBLICATIONS", the following has been left out: "Dean H. Hamer et al. patent application 'A Simian Virus Recombinant That Directs the Synthesis of Hepatitis B Surface Antigen'";

Col. 1, line 64, "possibility" is misspelled;

Col. 2, line 20, after "molecule", insert a period;

Col. 2, line 48, "diagrammatic" is misspelled;

Col. 2, line 52, "diagrammatic" is misspelled;

Col. 4, line 40, "HoaI" should be --HgaI--;

Col. 4, line 46, after "Fig. 2", insert a comma;

Col. 5, line 54, "o both" should be --of both--;

Col. 7, line 30, after "at", insert --37°C.--;

Col. 7, line 48, change "aci" to --acid--;

Col. 8, line 23, "sequence" is misspelled;

Col. 8, line 24, "sequence" is misspelled;

Col. 8, line 31, "sequence" is misspelled;

Col. 8, line 42, change the semi-colon after "(Fig. 3)" to a comma;

UNITED STATES PATENT AND TRADEMARK OFFICE
CERTIFICATE OF CORRECTION

PATENT NO. : 4,840,896
DATED : June 20, 1989
INVENTOR(S) : Vermuri B. Reddy et al.

It is certified that error appears in the above-identified patent and that said Letters Patent is hereby corrected as shown below:

Col. 8, line 49, "SaII" should be --SalI--;

Col. 8, line 58, "sequence" is misspelled;

Col. 8, line 59, "sequence" is misspelled;

Col. 9, line 23, "generally" is misspelled;

Col. 9, line 27, "sequence" is misspelled;

Col. 9, line 30, "sequence" is misspelled at both occurrences;

Col. 9, line 32, "sequence" is misspelled;

Col. 9, line 64, after "SVVP1", insert a comma;

Col. 10, line 30, "alpha" should be --Alpha--;

Col. 10, line 58, "subsequent" is misspelled;

Col. 12, claim 6, line 17, "said" is misspelled.

Signed and Sealed this

Third Day of April, 1990

Attest:

HARRY F. MANBECK, JR.

Attesting Officer    Commissioner of Patents and Trademarks